United States Patent [19]

Pace-Asciak et al.

[11] Patent Number: 5,616,607
[45] Date of Patent: Apr. 1, 1997

[54] HEPOXILIN ANALOGS

[75] Inventors: Cecil R. Pace-Asciak, Toronto, Canada; Peter M. Demin, Moscow, Russian Federation

[73] Assignee: HSC Research and Development Limited Partnership, Toronto, Canada

[21] Appl. No.: 405,603

[22] Filed: Mar. 21, 1995

Related U.S. Application Data

[63] Continuation of Ser. No. 38,324, Mar. 29, 1993, abandoned.
[51] Int. Cl.$^6$ .................................................. A01N 43/02
[52] U.S. Cl. ......................... 514/430; 514/475; 514/530; 514/531; 548/954; 548/967; 548/968; 549/90; 554/13; 554/214; 560/124
[58] Field of Search .................... 554/214, 213; 560/124; 548/954, 967, 968; 514/430, 475, 530, 531

[56] References Cited

U.S. PATENT DOCUMENTS 3,775,432  11/1973  Siddall et al. ..................... 549/90

FOREIGN PATENT DOCUMENTS 3518271  11/1986  Germany.

OTHER PUBLICATIONS

Lapitskaya et al., "A Chemoselective Synthesis of Functionalized 1,4-Alkadiynes (Skipped Diacetylenes)", Synthesis, pp. 65–66, Jan. 1993.
Demin et al., Chem. Abstracts 113: 402.51x, 1990.
Pace-Asciak, Chem. Abstracts 105: 58399q, 1986.
Corey et al., Tetrahed. Lett. 24:(95) "Total Synthesis of 12–(S)–10–hydroxy–trans–11, 12–epoxyeicosa–5,9, 14–(Z)–trienoic acids, Metabolites of areachidonic acid in mammalian blood Plateletes", 4913–4916, 1983.
Sun Lumin et al., Tetrahed. Lett. "Palladium Mediated Allylic Mitsunobu Displacement: Stereocontrolled Sythesis of Hepoxilin $A_3$ Trioxilin, $A_3$ Methyl Esters" 33(16) 2091–2094, 1992.
Demin et al., Chem. Abstracts 114: 42306g, 1991.
Demin et al., Tetrahed. Lett. 34(27), "Synthesis of Racemic 11,12–cyclopropyl analogs–of Hepoxilins $A_3$ and $B_3$", 4305–4308, 1993.

Shimizu and Wolfe, "Arachidronic Acid Cascade and Signal Transduction" J. Neurochem 55:1–15, 1990.
Pace–Asciak and Nigam, "Hepoxilins modulate second messenger systems in the Human Neutrophil," Cell–Cell Interactions in the Release of Inflammatory Mediators, 133–134, 1991.
Pace–Asciak et al., "A glutathione conjugate of hepoxilin $A_3$: Formation and action in the rat central nervous system", Proc. Natl. Acad. Sci. USA 87:3037–3041, 1990.

Primary Examiner—Porfirio Nazario-Gonzalez
Assistant Examiner—Dwayne C. Jones
Attorney, Agent, or Firm—Dinsmore & Shohl LLP

[57] ABSTRACT

Compounds of the general structure

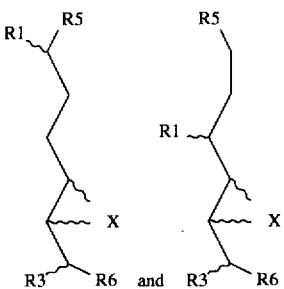

are disclosed, wherein X is O, $C_n$, NH, or S, wherein n is 1, 2, 3 or 4; R1 is OH, $CH_3$, $CH_2OH$, $N_3$ or $CH_2N_3$; R3 is H or $CH_3$; R5 is Y-R2, wherein Y is a six-carbon chain optionally containing up to three double or triple bonds or a mixture of double and triple bonds up to a maximum of three; R2 is $C_1$-$C_{10}$ alkyl OH, $C_1$-$C_{10}$ alkyl $N_3$ or COOR4, wherein R4 is H, a branched or unbranched $C_1$-$C_{10}$ alkyl (including substituted alkyl radicals), cycloalkyl, preferably $C_5$ or $C_6$ cycloalkyl, or a five- or six-membered aryl radical (including substituted aryl radicals), i.e. R2 is COOH or an ester of R4; R6 is a seven-carbon chain optionally containing up to three double or triple bonds or a mixture of double and triple bonds up to a maximum of three; and ...... indicates a single, double or triple bond. The compounds are analogs of hepoxilins and are used to modulate hepoxilin activity, for example in the control of inflammation or other processes mediated by intracellular calcium levels.

21 Claims, 1 Drawing Sheet

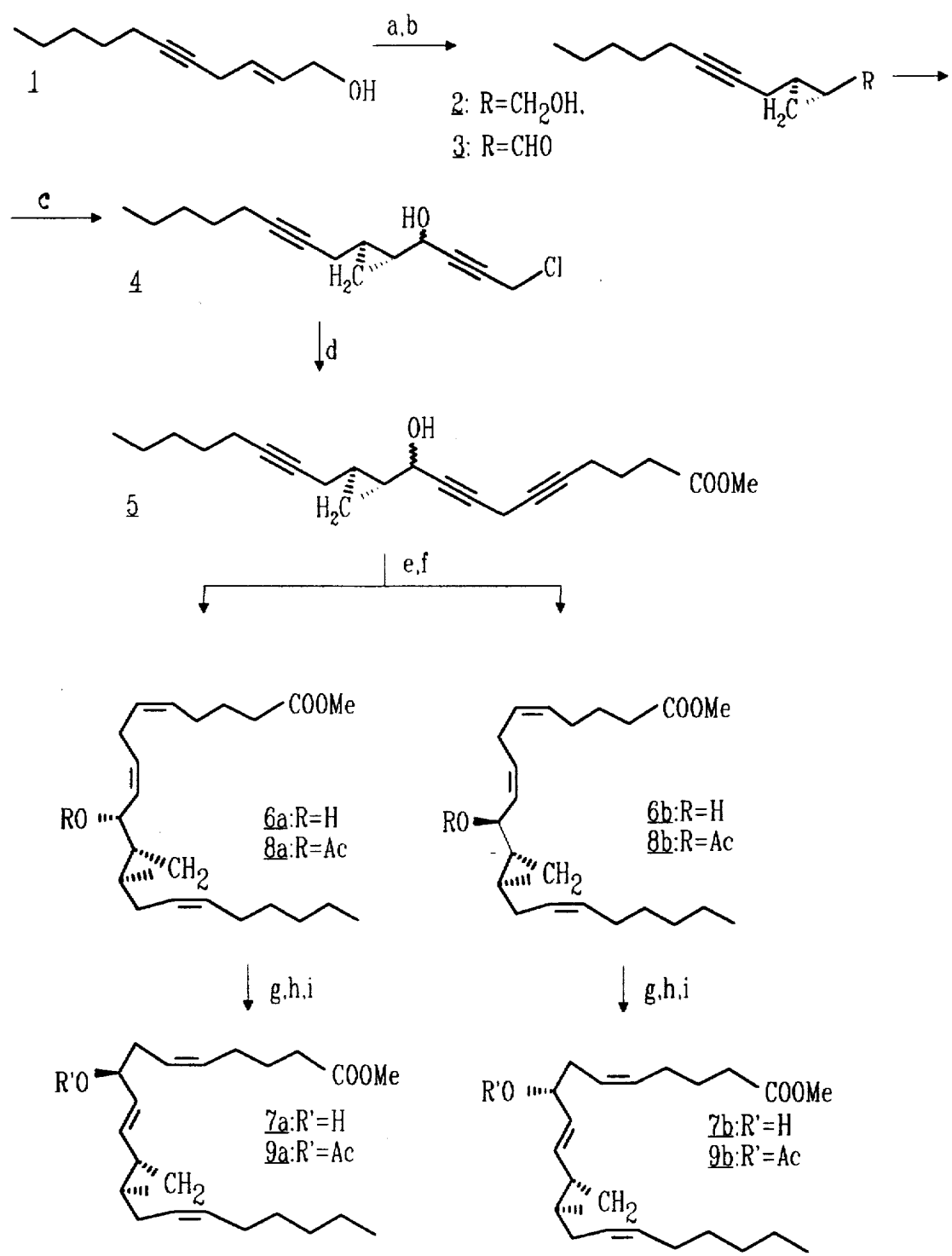
FIGURE

HEPOXILIN ANALOGS

This is a Continuation of application Ser. No. 08/038,324, filed Mar. 29, 1993, now abandoned on Mar. 21, 1995.

BACKGROUND OF THE INVENTION

It has become increasingly clear that second messengers play an important role in maintaining homeostasis in a diverse number of metabolic processes. Calcium is an important member of the group of second messengers, and regulation of calcium has become a focal point for investigating and controlling metabolic pathways and pathological conditions that can result from the aberrant regulation of these pathways. Regulation is achieved by opening or closing gated ion channels. This results in a change in the intracellular ion concentration in either of two ways: 1) changing the voltage across the plasma membrane or 2) allowing a major influx of ions, both generating an intracellular response. Calcium-regulated cell signaling pathways regulate cellular functions such as inflammation and smooth muscle contraction.

Inflammation is the body's reaction to injury. The inflammatory response involves three stages: first, an increase of blood flow to the injured area; second, an increase of capillary permeability caused by the retraction of endothelial cells lining vessel walls; and third, leucocyte migration to the site of injury. The third stage, known as chemotaxis, is a complex process that results in phagocytosis of invading agents by certain types of leucocytes such as the neutrophil. The neutrophil plays a key role in the body's response in inflammatory events such as infection. Once having arrived at the site of inflammation, the neutrophil is "activated" and releases a plethora of oxidative enzymes, known as a respiratory burst, that aid in destroying the invasive agent. An increase in intracellular calcium is thought to be involved in the initiation of the events that result in respiratory burst.

One group of compounds that have been shown to increase the influx of intracellular calcium in neutrophils is the "hepoxilins". Hepoxilins are products of an arachidonic acid pathway and have been implicated in the mediation of inflammation and smooth muscle contraction by modulation of second messenger calcium in response pathways. Hepoxilins are biologically active hydroxy epoxide derivatives of arachidonic acid formed through the 12-lipoxygenase pathway (Pace-Asciak et al., *J. Biol. Chem.* 258: 6835–6840, 1983; Pace-Asciak, *Biochim. Biophys. Acta* 793: 485–488, 1984; Pace-Asciak et al., *Prostaglandins* 25: 79–84, 1983). They are formed from 12-HPETE, an unstable hydroperoxide derivative of arachidonic acid (Pace-Asciak, *J. Biol. Chem.* 259: 8332–8337, 1984; Pace-Asciak et al., *Adv. Prostal. Throm. Leuk. Res.* 11: 133–134, 1983). Two hepoxilins have been isolated: hepoxilin $A_3$ [ (S, R)-hydroxy-11(S),12(S)-epoxy-eicosa-5Z, 9E, 14Z-trienoic acid] and hepoxilin $B_3$ [10(S, R)-hydroxy-11(R),12(S)-epoxy-eicosa-5Z, 8Z, 14Z-trienoic acid]. The term "hepoxilin" was coined in an attempt to combine aspects of structure with their first, though not necessarily their most important, demonstrated biological activity of insulin release (Pace-Asciak and Martin, *Prostgl. Leukotriene and Med.* 16: 173–180, 1984).

Hepoxilin A3 epimers are represented as:

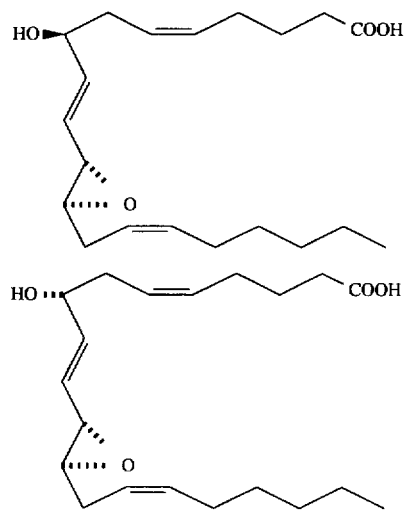

Hepoxilin B3 epimers are represented as:

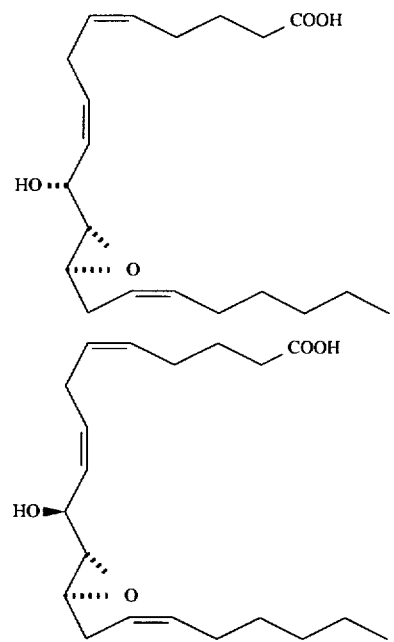

Hepoxilins are probably formed wherever 12-lipoxygenase is present because 12-HPETE is actively transformed into the hepoxilins by a variety of ferriheme proteins. Hence, ferriprotoporphyrin and such containing groups in proteins catalyze this transformation (Pace-Asciak et al., *Biolog. Oxidation Systems*, Eds C.C. Reddy et al., Academic Press, New York, 725–735, 1990). Hepoxilins are formed by platelets (Bryant and Bailey, *Prostaglandins* 17: 9–18, 1979; Jones et al., *Prostaglandins* 16: 583–590, 1978), lung (Pace-Asciak et al., *Biochim. Biophys. Acta* 712: 142–145, 1982), pancreatic islets (Pace-Asciak and Martin, ibid. 1984), brain (Pace-Asciak, ibid. 1988), aorta (Laneuville et al., *Biochim. Biophys. Acta* 1084: 60–68, 1991) and neutrophils (Dho et al., *Biochem. J.* 266: 63–68, 1990). Hepoxilin $B_3$ has been isolated from marine red algae (Moghaddam et al., *J. Biol. Chem.* 265: 6126–6130, 1990) and hepoxilin $A_3$ has been detected in the *Aplysia* brain (Piomelli et al., *Proc. Natl. Acad. Sci. USA* 86: 1721–1725, 1989). Hepoxilins are also formed by the rat pineal gland (Reynaud et al., unpublished observations).

Hepoxilins have been shown to possess a variety of biological actions related to their ability to affect ion fluxes in the cell. Hepoxilins raise intracellular calcium in human neutrophils (Dho et al., *Biochem. J.* 266: 63–68, 1990), increase the transport of calcium across membranes (Derewlany et al., *Can. J. Physiol. Pharmacol.* 62: 1466–1469, 1984), stimulate the release of insulin (Pace-Asciak and Martin, ibid. 1984), and regulate the volume of human platelets through an effect on potassium channels in the cell (Margalit et al. 1993 *Proc. Natl. Acad. Sci. USA*, in press). Biological actions of the hepoxilins demonstrated so far include the potentiation of aortic and tracheal vasoconstriction (Laneuville et al, *Br. J. Pharmacol.* 105: 297–304, 1992; 107: 808–812, 1992), potentiation of vascular permeability (Laneuville and Pace-Asciak, *Prostaglandins, Leukotrienes, Lipoxins and PAF*. Ed. J. M. Bailey, Plenum Press New York: 335–338, 1991), modulation of second messenger systems (Nigam et al., *Biochem. Biophys. Res. Comm.* 171: 944–948, 1990), regulation of cell volume (Margalit et al. *Proc. Natl. Acad. Sci. USA*, 1993, in press) and modulation of neurotransmission (Carlen et al., *Brain Res.* 497: 171–176, 1989; Piomelli et al., *Proc. Natl. Acad. Sci USA* 86: 1721–1725, 1989; and Pace-Asciak et al., *Proc. Natl. Acad. Sci. USA* 87: 3037–3041, 1990).

In view of the role of the hepoxilins in regulating physiological processes, a means for regulating hepoxilin action is needed. Hepoxilin antagonists find utility in reducing inflammation, asthma, hypertension, migraine and septic shock and in modulating other processes mediated by cellular calcium levels. Hepoxilin agonists find utility in diabetes.

BRIEF DESCRIPTION OF THE DRAWING

The FIGURE illustrates a synthetic scheme for certain hepoxilin analogs.

DETAILED DESCRIPTION OF THE INVENTION

The present invention provides hepoxilin analogs that modulate the mobilization of intracellular calcium in human neutrophils induced by such agonists as f-Met-Leu-Phe (fMLP), platelet activation factor (PAF), leukotriene $B_4$ (LTB4), hepoxilin $A_3$ and thapsigargin. Certain of these analogs (including 11,12-cyclopropyl analogs) have been found to antagonize hepoxilin activity in experimental models. As such they may be useful in the modulation of hepoxilin-mediated (or hepoxilin agonist-mediated) processes, including inflammation associated with neutrophil activation in inflammatory disease.

Broadly speaking, the present invention is directed to hepoxilin analogs having the general structure I or II:

I

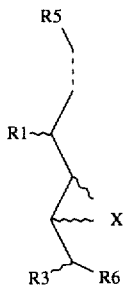

II

Within structures I and II: X is O, $C_n$, NH, or S, wherein n is 1, 2, 3 or 4; R1 is OH, $CH_3$, $CH_2OH$, $N_3$ or $CH_2N_3$; R3 is H or $CH_3$; R5 is Y-R2, wherein Y is a six-carbon chain optionally containing up to three double or triple bonds or a mixture of double and triple bonds up to a maximum of three; R2 is $C_1$-$C_{10}$ alkyl OH, $C_1$-$C_{10}$ alkyl $N_3$ or COOR4, wherein R4 is H, a branched or unbranched $C_1$-$C_{10}$ alkyl (including substituted alkyl radicals), cycloalkyl (including substituted cycloalkyl), preferably $C_5$ or $C_6$ cycloalkyl, or a five- or six-membered aryl radical (including substituted aryl radicals), i.e. R2 is COOH or an ester of R4; R6 is a seven-carbon chain optionally containing up to three double or triple bonds or a mixture of double and triple bonds up to a maximum of three; and ...... indicates a single, double or triple bond; subject to the limitation that when the structure is

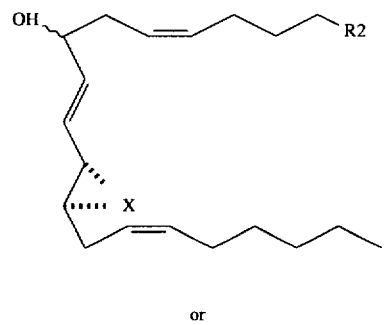

or

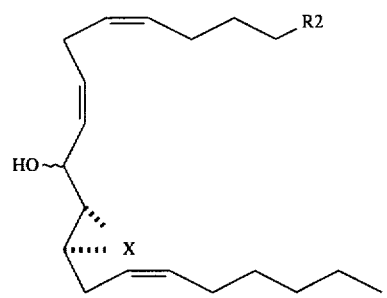

and R2 is COOH or $COOCH_3$, then X is not O.

Within one embodiment, the hepoxilin analogs of the present invention are of the following structures III–IV:

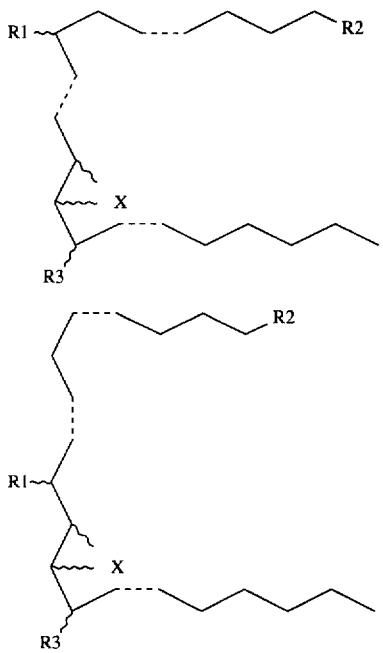

wherein structures V–VI are preferred:

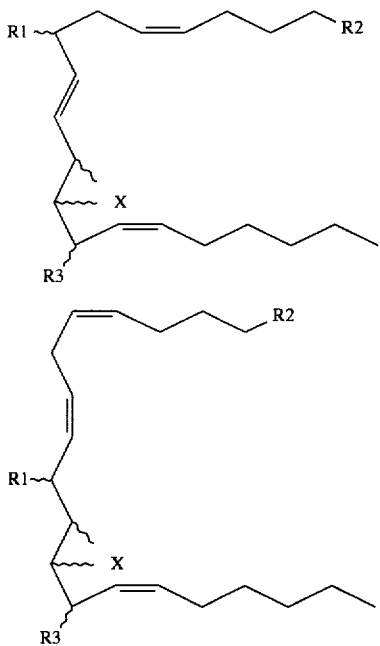

Within structures III–VI, R1, R2, R3, R4 and X are as previously defined, subject to the limitation that if R1 is OH, R2 is COOH or COOCH$_3$, and R3 is H, then X is not O. Preferred substitutions within R4 include lower alkyl and halo.

Unless otherwise specified, the term "alkyl" is used herein to refer to branched and unbranched alkyl radicals. Suitable alkyl radicals include methyl, ethyl, n-propyl, isopropyl, n-butyl, tert-butyl, n-amyl, sec-amyl, n-hexyl, 2-ethylbutyl, 2,3-dimethylbutyl and the like. Lower alkyl ($C_1$-$C_6$ alkyl) radicals are preferred, such as methyl and ethyl radicals. The term "alkenyl" refers to branched and unbranched hydrocarbon chains having one or more double bonds, including mono-unsaturated and poly-unsaturated radicals. Lower alkenyl radicals having from one to six carbon atoms are preferred. The term "alkynyl" refers to branched and unbranched hydrocarbon chains having one or more triple bonds, including mono-unsaturated and poly-unsaturated radicals. Lower alkynyl radicals having from one to six carbon atoms are preferred. The term "aryl" includes monocyclic aromatic hydrocarbon radicals. Suitable aryl groups include phenyl, chlorophenyl, benzyl and the like. The term "halo" includes chloro, fluoro, bromo and iodo. The symbol . . . . . . is used to indicate a bond that can be single, double or triple.

Preferred epimers of hepoxilin analogs III–VI include the following:

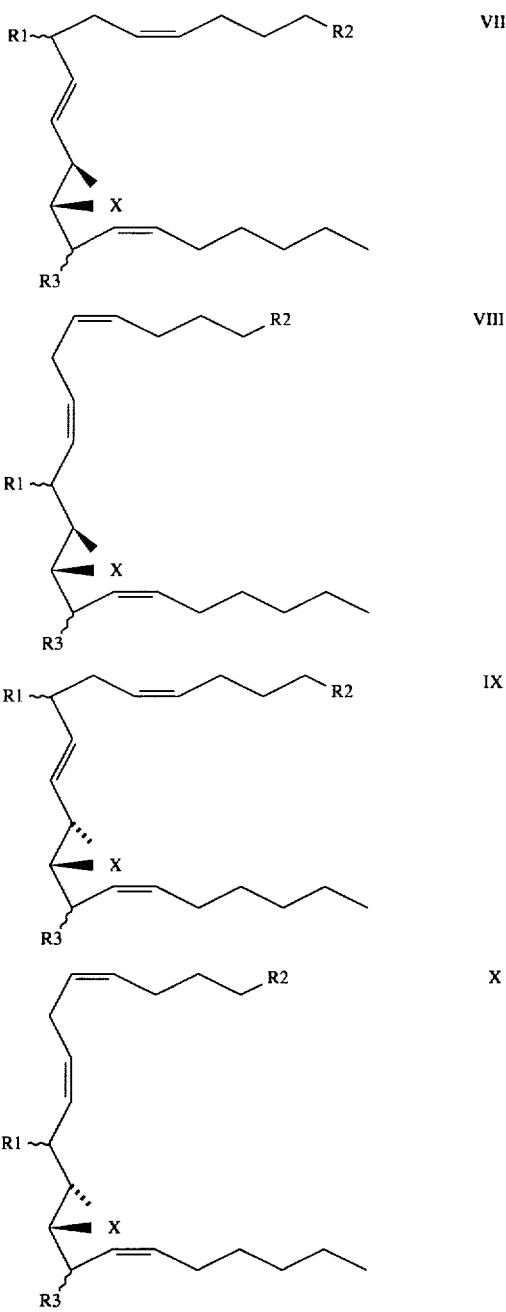

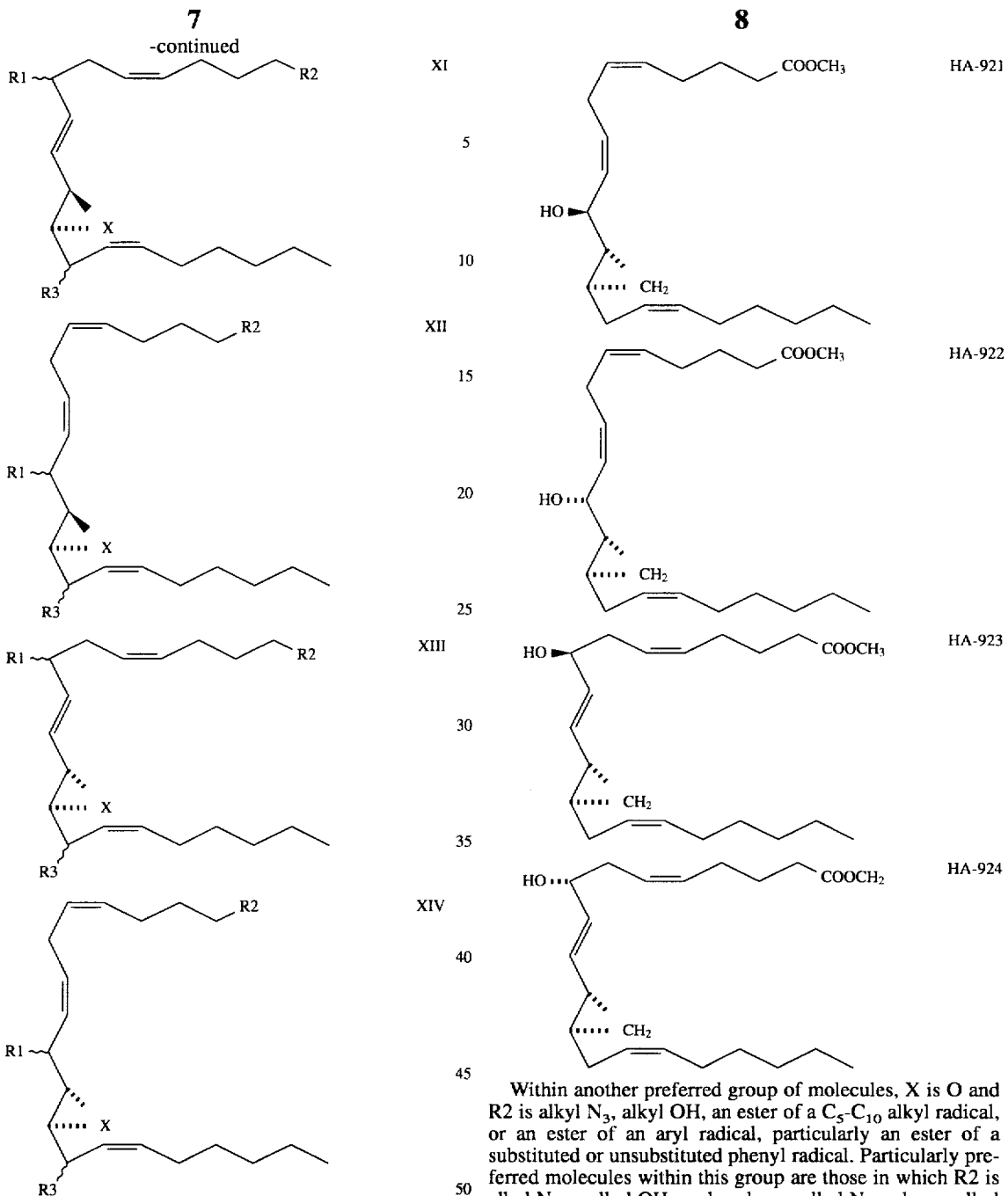

Within the compounds represented by structures III–XIV, X is preferably NH, S or $C_n$, wherein n is 1, 2, 3 or 4; R1 is OH, $CH_3$, $CH_2OH$, $N_3$ or $CH_2N_3$; R2 is COOH or $COOCH_3$; and R3 is H, $CH_3$ OR $CH_2OH$. When X is $C_n$, X and carbon atoms 11 and 12 will form a three- to six-membered ring, optionally containing one or more double bonds, or an aromatic ring. Within these molecules it is particularly preferred that R1 is OH; X is $C_n$, wherein n is most preferably 1, forming a cyclopropane ring; and R3 is H.

Within another preferred group of molecules, X is $C_n$, NH or S; R1 is OH; R2 is COOR4; R3 is H or $CH_3$; and R4 is H or lower alkyl, particularly methyl. Particularly preferred compounds within this group are those in which R1=OH; X=$CH_2$; R2=COOH or $COOCH_3$; and R3=H, including those molecules designated as HA-921, HA-922, HA-923 and HA-924.

Within another preferred group of molecules, X is O and R2 is alkyl $N_3$, alkyl OH, an ester of a $C_5$-$C_{10}$ alkyl radical, or an ester of an aryl radical, particularly an ester of a substituted or unsubstituted phenyl radical. Particularly preferred molecules within this group are those in which R2 is alkyl $N_3$ or alkyl OH, such as lower alkyl $N_3$ or lower alkyl OH.

According to the present invention, structural analogs of hepoxilins, including the representative hepoxilin antagonists methyl 8-hydroxy-11,12-cyclopropyl-5(Z), 9(E), 14(Z)-eicosatrienoate ($\Delta HxA_3$) and methyl 10-hydroxy-11,12-cyclopropyl-5(Z),8(Z),14(Z)-eicosatrienoate ($\Delta HxB_3$), may conveniently be synthesized utilizing the acetylenic approach to hepoxilins (Demin et al., *Bioorg. Khim* 16:1125–1133, 1990).

A synthetic scheme for hepoxilin antagonists is set forth in the FIGURE. As shown therein, 1-hydroxyundeca-2(E)-en-5-yne (1), a common intermediate in this synthetic scheme, prepared as described (Demin et al., ibid.), is modified to obtain the corresponding three-membered cyclopropane ring- containing alcohols, which are the key synthons to hepoxilin analogs. According to this scheme, alcohol (1) [1-Hydroxyundeca-2(E)-en-5-yne] is treated with $CH_2I_2$ and Zn-Cu couple in dry ether giving racemic (2S*,3S*)-2,3-cyclopropylalcohol (2), which is then oxidized to aldehyde (3) with pyrydinium dichromate. Two subsequent condensations of aldehyde (3) with Li-derivative of propargyl chloride leads to cyclopropylcarbinol (4). $^1$H-NMR spectrum at this stage shows a 7:3 ratio between two diastereomers. Propargylic chloride (4) is reacted with methyl hexynoate in the presence of equimolar amounts of CuI and NaI in DMF in the presence of $K_2CO_3$, 10 hours at 20° C., resulting in the triacetylenic analog of $\Delta HxB_3$ (5) obtained as an inseparable mixture with the same epimeric ratio. Following selective hydrogenation of the triacetylenic analog (5) on Lindlar catalyst in the presence of 2 equivalents of quinoline and subsequent separation, two $C^{10}$-epimers of more and less polar $\Delta HxB_3$ methyl esters (6a,b) are obtained in a 7:3 ratio as a colorless oil. The same ratio between more and less polar epimers is obtained for native $HxB_3$ methyl esters when similar condensations of appropriate aldehyde with Li-derivative of terminal acetylene are used (Demin et al., ibid.]. The same relative configuration for more and less polar $\Delta HxB_3$ is thus expected. This proposition is confirmed by the consideration of NMR spectra of individual $\Delta HxB_3$ methyl esters (6a, 6b). NMR spectra show the two differences between epimers: coupling constant $J_{10,11}$ is larger for the more polar epimer (d, 7.8 Hz) than for the less polar epimer (d, J 7.3 Hz), and proton at $C^{11}$ of cyclopropyl group has less chemical shift (0.68 ppm) for the more polar epimer than for the less polar epimer (0.81 ppm). These data are in agreement with those described for $\alpha,\beta$-cyclopropylcarbinolic systems (Descotes et al., *Tetrahedron* 29:2931–2935, 1973). Furthermore, oxidation of both fully saturated $\Delta HxB$ ($\Delta HxB_0$) epimer and native saturated HxB ($HxB_0$) by pyrydinium dichromate into the corresponding ketones followed by treatment of the latter with sodium borohydride results, in both cases, in a mixture of initial $\alpha,\beta$-cyclopropyl- and $\alpha,\beta$-epoxycarbinols in a 1.7:1 ratio between less and more polar epimers. This ratio is similar to that described for reduction of $\alpha,\beta$-epoxyketones to $\alpha,\beta$-epoxycarbinols by $NaBH_4$ with preference of erythro- epoxycarbinol (Pierre et al., *Tetrahedron Lett.* (42): 4371–7374, 1972 and Nakata et al., *Tetrahedron Lett.* 22(47: 4723–4726, 1981).

On the basis of the foregoing considerations, it can be concluded that the more polar $\Delta HxB_3$ epimer (6a) has a threo, syn or (10S*,11R*,12S*)-configuration, and the less polar epimer of $\Delta HxB_3$ (6b) has a relative erythro, anti or (10R*,11R*,12S*)-configuration. In the case of cyclopropyl analogs of $HxB_3$, the absolute configuration of the carbinolic center is opposite to the configuration of native $HxB_3$, while the relative configuration remains the same (Demin et al., *Bioorg. Khim.* 16: 1125–1133, 1990).

To obtain the two $C^8$-epimeric $\Delta HxA_3$ methyl esters (7a,b), the stereocontrolled rearrangement of allylic acetates catalyzed by Pd(II) (Grieco et al., *J. Am. Chem. Soc.* 102: 7587–7588, 1980) is used. Treatment of individual $\Delta HxB_3$ acetates (8a, 8b) obtaining from (6a, 6b) with 0.1 eq. of $PdCl_2(MeCN)_2$ in THF leads to the mixtures of $\Delta HxB_3$ and $\Delta HxA_3$ acetates (8a, 9a) and (8b, 9b) in a ca. 1:1 ratio in both cases. These acetates can be separated from each other by high performance liquid chromatography (HPLC) on a straight phase column (μ Porasil or the like) using 0.3% isopropanol in hexane. Subsequent hydrolysis gives two individual $C^8$-epimers of $\Delta HxA_3$ (7a, 7b). On the basis of the $S_N2'$ reaction mechanism, the more polar $\Delta HxA_3$ (obtained from anti $\Delta HxB_3$) is referred to as syn or (8R*,11S*,12S*)-epimer (7b), and the less polar $\Delta HxA_3$ as anti or (8S*,11S*,12S*)-epimer (7a), respectively. The chromatographic properties of $\Delta HxA_3$ methyl esters (7a), (7b) are also similar to native $HxA_3$ methyl esters with known relative configuration (Demin et al., *Bioorg. Khim.*, 16: 571–572, 1990 and Corey et al., *Tetrahedron Lett.*: 31(15): 2113–2116, 1990).

The above-described procedures are modified as necessary to produce other hepoxilin analogs. The necessary alterations in starting materials, reactants and conditions will be evident to those skilled in the art. Thus, the methods described above can be employed for the production of hepoxilin analogs having alternative R groups and different degrees of saturation at specific carbon atoms. Individual epimers or mixtures may be produced as desired.

Within the present invention, hepoxilin analogs may be prepared in the form of pharmaceutically acceptable salts, especially acid-addition salts, including salts of organic acids and mineral acids. Examples of such salts include organic acids such as formic acid, acetic acid, propionic acid, glycolic acid, lactic acid, pyruvic acid, oxalic acid, succinic acid, malic acid, tartaric acid, citric acid, benzoic acid, salicylic acid, tris hydroxy amino methyl (THAM) and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention find utility in human and veterinary medicine for modulating the action of the hepoxilins. Hepoxilin antagonists may be administered for the treatment of such conditions as inflammation, asthma, hypertension, migraine and septic shock. In general, the compounds or their salts are formulated for enteral or parenteral administration by combining them with a pharmaceutically acceptable vehicle according to conventional procedures. See, *Remington's Pharmaceutical Sciences*, 18th ed., Gennaro, ed., Mack Publishing Co, Easton, Pa., 1990, incorporated herein by reference. The active ingredient will be combined with one or more diluents, fillers, emulsifiers, excipients, etc., and may be provided in such forms as liquids, powders, emulsions, tablets, capsules and the like. Such compositions may further include one or more auxiliary substances, including wetting agents, preservatives, stabilizers, buffers, lubricants, colorings, etc.

The following non-limiting examples are provided to illustrate certain embodiments of the invention.

EXAMPLE I

Instruments and Reagents

Referring to the FIGURE, vacuum distillation of compound (2) was done using a Kugelrohr apparatus (Aldrich, Milwaukee, Wis.) at the stated oven temperature. Thin layer chromatography was performed on aluminum sheets coated with silica gel 60 $F_{254}$, layer thickness 0.2 mm (Merck, Dharmstadt, Germany). Preparative HPLC was performed using a μ Porasil $SiO_2$ column, 7.8×300 mm (Waters, Milford, Mass.), using as eluent 0.8% i-PrOH in hexane for compounds (6a,b) and (7a,b), 0.3% i-PrOH in hexane for (8a,b) and (9a,b). GC analyses were carried out on a Hewlett-Packard 5700A gas chromatograph (Hewlett-Packard, Palo Alto, Calif.) using a glass capillary column, (SPB-1, Supelco, Bellefonte, Pa.) 60 m×0.3 mm. Electron impact mass spectra were obtained on a Hewlett-Packard GC MS using a fused silica methyl silicone capillary column (HP-1, 12 m×0.2 mm). Compounds (4), (5), (6a,b) and (7a,b) were injected onto the GC column as their tBDMSi derivatives prepared with a t-butyldimethylsilylimidazole-DMF kit (Supelco). $^1$H-NMR spectra were obtained on Bruker-AM500 (500 MHz) spectrometer (Bruker, Karlsruhe, Germany) in CDCl$_3$ with Me$_4$Si as an internal standard ($\delta$=0).

Pyridinium dichromate, Lindlar catalyst (Aldrich) and n-BuLi solution in hexane (Fluka, Buchs, Switzerland) were used as received. 1-Hydroxyundec-2(E)-en-5-yne (1) and 5-hexynoic acid were synthesized as described (Demin et al., *Bioorg. Khim.* 16: 1125–1133, 1990).

(2S*,3S*)-1-Hydroxy-2,3-Cyclopropyl-5-Yne (2)

A suspension of Zn-Cu couple (2.9 g) in dry ether (10 mL) in the presence of I$_2$ (0.1 g) was refluxed for 5 min until the red-brown color disappeared. Diiodomethane (2.95 g) was added, and the resulting mixture was stirred 1 h at 35° C. 1-Hydroxyundec-2(E)-en-1-yne (1; numbers refer to the synthetic scheme shown in the FIGURE) (0.33 g) in 5 mL of ether was added, and the reaction mixture was refluxed for 30 min with stirring. Saturated aqueous NH$_4$Cl was added, the mixture was extracted with ether, and the ether phase was dried over Na$_2$SO$_4$. After evaporation of the solvent, the residue was distilled in vacuo, yielding 279 mg (78%) of cyclopropyl alcohol (2), b.p. 100°–110° C. ($10^{-2}$ mm Hg). $^1$H-NMR (500 MHz, $\delta$, ppm): 0.43, 0.53 (dt, 1H, J 4.9 and 8.5 Hz, cyclopropyl-H), 0.84, 1.05 (m, 2H, H$^2$+H$^3$), 0.90 (t, 3H, J 7.0 Hz, H$^{11}$), 1.33 (m, 4H, H$^9$+H$^{10}$), 1.48 (quintet, 2H, J 7.22 Hz, H$^8$), 2.14 (tt, 2H, J 2.4 and 7.2 Hz, H$^7$), 2.19 (dt, 0.5 H, J 2.4 and 6.0 Hz, H$^4$), 2.23 (dt, 0.5 H, J 2.4 and 6.0 Hz, H$^4$), 2.32 (dt, 0.5 H, J 2.4 and 5.5 Hz, H$^4$), 2.35 (dt, 0.5 H, J 2.4 and 5.5 Hz, H$^4$), 3.46 (m, 2H, H$^1$). Mass spectrum (m/z, % of related intensity): 162 ([M–H$_2$O]$^+$, 0.4) 109 ([M–C$_4$H$_9$]$^+$, 25), 95 ([M–C$_5$H$_{11}$]$^+$, 34), 91 ([M–C$_4$H$_9$–H$_2$O]$^+$, 67), 79 (100 ), 77 ([M–C$_5$H$_{11}$–H$_2$O]$^+$, 52).

(2R*,3S*)-2,3-Cyclopropyl-5-Yn-1-Al (3)

To a suspension of Py$_2$H$_2$Cr$_2$O$_7$ (85 mg) and molecular sieves 3 Å (Aldrich) (120 mg) in 3 mL of dry CH$_2$Cl$_2$, 10 µl of AcOH and cyclopropyl alcohol (2) in 0.5 mL of CH$_2$Cl$_2$ was added. After 30 min, the reaction was quenched by addition of 20 µl of isopropanol, and the mixture was filtered through silica gel and eluted with hexane. Evaporation of the solvent gave 18.2 mg (92%) of aldehyde (3). $^1$H-NMR (500 MHz, $\delta$, ppm): 0.89 (t, 3H, J 6.9 Hz, H$^{11}$), 1.15, 1.30 (m, 2H, cyclopropyl-H), 1.33 (m, 4H, H$^9$+H$^{10}$), 1.48 (quintet, 2H, J 7.1 Hz, H$^8$), 1.65, 1.88 (m, 2H, H$^2$+H$^3$), 2.12 (tt, 2H, J 2.2 and 7.1 Hz, H$^7$), 2.45 (m, 2H, H$^4$), 9.13 (d, 1H, J 5.3 Hz, H$^1$). Mass-spectrum (m/z) % of related intensity): 177 ([M–1]$^+$, 0.4), 149 ([M–CHO]$^+$, 5.0), 121 ([M–C$_4$H$_9$]$^+$, 10), 107 ([M–C$_5$H$_{11}$]$^+$, 25), 93 ([M–C$_4$H$_9$–CHO+H]$^+$, 29), 79 ([M–C$_5$H$_{11}$–CHO+H]$^+$, 47) 69 (100).

(4S*, 5R*, 6S*)- and (4R*, 5R*, 6S*)-1-Chloro-4-Hydroxy-5,6-Cyclopropyltetradeca-2,8-Diynes (4)

A solution of propargyl chloride (1.6 g) in dry ether (100 mL) was cooled to –78° C., and n-BuLi (1.38 g, 21.6 mL of 1.5M in hexane) was added over a period of 15 min. The mixture was stirred for 30 min at –78° C., and aldehyde (3) (0.77 g) in 20 ml of ether was added. After 15 min, 20 ml of H$_2$O was added to quench the reaction, and the mixture was warmed to 20° C. The ether layer was separated, the residue was extracted with ether, the combined extracts were dried over Na$_2$SO$_4$, and the solvent was evaporated to dryness resulting in an orange oil which was absorbed on a silica gel column. Elution with 10% EtOAc in hexane and solvent removal gave an epimer mixture of racemic α, β-cyclopropyl alcohols (4) as a colorless oil (0.91 g, 84%, epimer ratio 7:3 by $^1$H-NMR analysis); $^1$H-NMR (500 MHz, $\delta$, ppm); 0.57–0.69 (m, 2H, cyclopropyl-H), 0.90 (t, 3H, J 7.1 Hz, H$^{14}$), 1.03, 1.09 (m, 1H, H$^5$), 1.19 (m, 1H, H$^6$), 1.32 (m, 4H, H$^{12}$+H$^{13}$), 1.48 (quintet, 2H, J 7.2 Hz, H$^{11}$), 1.89 (d, 1H, J 6.4 Hz, OH), 2.13 (tt, 2H, J 7.2 and 2.4 Hz, H$^{10}$), 2.22–2.40 (m, 2H, H$^7$), 4.15 (t, 2H, J 2.3 Hz, H$^1$), 4.28 (m, 0.3H, H$^4$), 4.35 (m, 0.7H, H$^4$). Mass spectrum of the tBDMSi . derivative (m/z, % of related intensity): 365 ([M–1]$^+$, 0.15), 331 ([M–Cl]$^+$, 1.9), 309 ([M–t-Bu]$^+$, 5.0), 275 ([M–t-Bu–Cl+H]$^+$, 6.8) 199 ([M–Cl–tBDMSi]$^+$, 24), 129 ([M–C$_5$H$_{11}$–Cl–t-BuMe$_2$SiOH+H]$^+$, 92), 128 (100).

Methyl (10S*, 11R*, 12S*)- and (10R*, 11R*, 12S*)-10-Hydroxy-11,12-Cyclopropyleicosa-5,8,14-Triynoates (5)

To a suspension of anhydrous CuI (490 mg), NaI (774 mg) and K$_2$CO$_3$ (712 mg) in DMF (50 mL), the solutions of methyl 5-hexynoate (390 mg in 5 mL of DMF) and propargylic chloride (4) (650 mg in 5 mL of DMF) were successively added. The mixture was stirred overnight at 20° C., then saturated aqueous NH$_4$Cl solution (200 mL) was added. After extraction with ether, the organic layer was dried by Na$_2$SO$_4$, and the solvent was evaporated to dryness. Subsequent filtration of the resulting oil through silica gel (eluent 15% EtOAc in hexane) afforded triyne (5) as a yellow oil (740 mg, 84%, epimer ratio 7:3 by $^1$H-NMR analysis). $^1$H-NMR (500 mHz, $\delta$, ppm): 0.57, 0.64 (m, 2H, cyclopropyl-H), 0.90 (t, 3H, J 7.0 Hz, H$^{20}$), 1.00–1.22 (m, 2H, H$^{11}$+H$^{12}$), 1.33 (m, 4H, H$^{18}$+H$^{19}$), 1.48 (quintet, 2H, J 7.1 Hz, H$^{17}$), 1.82 (quintet, 2H, J 7.2 Hz, H$^3$), 2.13–2.25 (m, 6H, H$^4$+H$^{13}$+H$^{16}$), 2.44 (t, 2H, J 7.44 Hz, H$^2$), 3.15 (quintet, 0.8H, J 2.3 Hz, H$^7$), 3.30 (br.t., 0.2H, J 2.3 Hz, H$^7$), 3.68 (s, 3H, COOMe), 4.26 (dt, 0.3H, J 6.4 and 1.3 Hz, H$^{10}$), 4.32 (dt, 0.7H, J 6.1 and 1.9 Hz, H$^{10}$). Mass spectrum of the tBDMS derivative (m/z, % of related intensity): 455 ([M–1]$^+$, 0.15), 425 ([M–OMe]$^+$, 0.19), 399 ([M–t-Bu]$^+$, 37), 293 ([C$^{10}$-C$^{20}$]$^+$, 3.7), 317 ([C$^8$-C$^{20}$]$^+$, 0.90), 307 ([C$^1$-C$^{10}$]$^+$, 0.80), 221 (64), 189 ([(C$^1$-C$^{11}$)–t-BuMe$_2$SiOH+H]$^+$, 17), 75 (100).

Methyl (10S*, 11R*, 12S*)- and (10R*, 11R*, 12S*)-10-Hydroxy, 11,12-Cyclopropyl-5(Z),8(Z),14(Z)-Eicosatrienoates (6a,b)

A solution of triyne (5) (120 mg) in dry benzene (2 mL) was added to a mixture of hydrogenpresaturated Lindlar catalyst (100 mg) and quinoline (1000 µl) in 10 ml of benzene, and the resulting mixture was stirred until hydrogen consumption was completed (60 min, 10 mL of H$_2$ was absorbed). The poisoned catalyst was filtered off, and the filtrate was added to a new portion of hydrogen-presaturated Lindlar catalyst (100 mg) and quinoline (200 µl). After hydrogen consumption was stopped the procedure was repeated twice. During this procedure, the reaction mixture was analyzed by GC-MS as the tBDMSi derivative monitoring the prominent ion m/z 405 [M–t-Bu]$^+$. After the reaction was completed (total hydrogen absorption 79.4 mL, 340% of theoretical amount), GC MS analysis of the reaction mixture showed 92% conversion into the desirable trienes (6a, b). The catalyst was filtered off, the filtrate was poured onto an aluminum oxide column (pH 6.9–7.1). Quinoline was removed with 5% EtOAc in hexane. The column was then eluted with EtOAc, giving a yellow oil (115 mg) containing 95% trienes (6a,b) (evaluated by GLC analysis of tBDMSi derivative). Individual epimers (6a), (6b) were separated using HPLC (µPorasil 7.8×300 mm, Waters), eluent 1.0% i-PrOH in hexane, UV- detection at 210 nm. More polar epimer (6a): a colorless oil, 55 mg yield (46%). Rf 0.39 (C$_6$H$_6$-Et$_2$O, 85:15, 3 developments), $^1$H-NMR-spectrum (500 MHz, $\delta$, ppm): 0.39 (dt, 1H, J 4.8 and 8.1 Hz, cyclopropyl-H), 0.53 (dt, 1H, J 4.8 and 8.5 Hz, cyclopropyl-H), 0.68 (m, 1H, $H^{11}$), 0.83 (m, 1H, $H^{12}$), 0.87 (t, 3H, J 6.8 Hz, $H^{20}$), 1.26–1.36 (m, 6H, $H^{17}+H^{18}+H^{19}$), 1.63 (br. s., 1H, OH), 1.70 (quintet, 2H, J 7.5 Hz, $H^3$), 1.90–2.12 (m, 6H, $H^4+H^{13}+H^{16}$), 2.32 (t 2H, J 7.5 Hz, $H^2$), 2.75 (m, 1H, $H^7$), 2.86 (m, 1H, $H^7$), 3.67 (s, 3H, COOMe) 3.95 (ddd, 1H, J 1.0, 7.8 and 7.8 Hz, $H^{10}$), 5.36–5.50 (m, 6H, olefinic H). Mass spectrum, tBDMSi derivative (m/z, % of related intensity): 462 ([M]$^+$, 0.06), 431 ([M−OMe]$^+$, 0.80), 405 ([M−t-Bu]$^+$, 37), 324 ([$C^1$-$C^{11}$]$^+$, 20), 211 (12), 169 (12), 105 (21), 75 (100). Less polar epimer (6b): a colorless oil, 30 mg yield (25%). $R_f$ 0.51 ($C_6H_6$-$Et_2O$, 85:15, 3 developments), $^1$H-NMR-spectrum (500 MHz, δ, ppm): 0.33 (dt, 1H, J 5.1 and 8.4 Hz, cyclopropyl-H), 0.43 (dt, 1H, J 5.1 and 8.4 Hz, cyclopropyl-H), 0.81 (m, 2H, $H^{11}+H^{12}$), 0.89 (t, 3H, J 6.7 Hz, $H^{20}$), 1.25–1.36 (m, 6H, $H^{17}+H^{18}+H^{19}$), 1.58 (d, 1H, J 3.2 Hz, OH), 1.70 (quintet, 2H, J 7.4 Hz, $H^3$), 1.96–2.10 (m, 6H, $H^4+H^{13}+H^{16}$), 2.31 (t, 2H, J 7.4 Hz, $H^2$), 2.74, 2.84 (m, 2H, $H^7$), 3.67 (s, 3H , COOMe), 3.97 (ddd, 1H, J 3.0, 7.3, and 7.3 Hz, $H^{10}$), 5.36–5.48 (m, 6H, olefinic H). Mass spectrum, tBDMSi derivative (m/z, % of related intensity): 462 (0.04), 431 (0.35), 405 (20), 334 (4.7), 324 (2.8), 215 (4.2), 211 (3.0), 169 (6.0), 105 (26), 75 (100). Methyl (8S*, 11S*, 12S*)- and (8R*, 11S*, 12S*)-8-Hydroxy-11,12-Cyclopropyl-5(Z), 9(E), 14(Z)-Eicosatrienoates (7a, b)

A mixture of triene (6a), (6b) (10 mg of each epimer), acetic anhydride (150 μl), and pyridine (450 μl) was maintained at 20° C. overnight. The mixture was evaporated to dryness, and the residue was purified by HPLC using 0.8% i-PrOH in hexane as eluent. The resulting allylic acetates (8a), (8b) were treated separately with a catalytic amount of freshly prepared bis(acetonitrile)palladium(II) chloride (0.6 mg, 0.1 equiv) in dry THF (10 mL) during 3 h at 20° C. THF was evaporated, and the residue was passed through an $Al_2O_3$ column (pH 6.9–7.1) using EtORc as eluent. The resulting yellow oil contained a mixture of acetates ΔHxA$_3$ (7a), (7b) and ΔHxB$_3$ (6a), (6b) (ratio 1.2:1 from more polar ΔHxB$_3$ (HA-922) epimer (6a) and 0.9:1 from less polar ΔHxB$_3$ (HA-921) epimer (6b) by HPLC analysis). Acetates were separated by HPLC using 0.3% i-PrOH in hexane as eluent, yield of (9a) was 5.8 mg, 58% (from more polar ΔHxB$_3$ (6a)), and (9b) was 3.8 mg, 38% (from less polar ΔHxB$_3$ (6b)); ΔHxA$_3$ acetates (9a), (9b) were non-separable from each other by HPLC or by TLC. $^1$H-NMR spectrum (any epimer, 500 MHz, δ, ppm): 0.57 (m, 2H, cyclopropyl-H), 0.80, 1.15 (m, 2H, $H^{11}$ and $H^{12}$), 0.88 (t, 3H, J 6.91 Hz, $H^{20}$), 1.28–1.32 (m, 6H, $H^{17}+H^{18}+H^{19}$), 1.69 (quintet, 2H, J 7.4 Hz, $H^3$), 1.99–2.07 (m, 6H, $H^2+H^4+H^{16}$), 2.01 (s, 3H, OAc), 2.32 (m, 4H, $H^7+H^{13}$), 2.37 (dt, 1H, J 7.0 and 7.2 Hz, $H^8$), 3.67 (s, 3H, COOMe), 5.19 (dt, 1H, J 6.7 and 6 8 Hz, $H^6$), 5.29 (dd, 1H, J 8.7 and 15.5 Hz, $H^{10}$), 5.38 (m, 3H, $H^5+H^{14}+H^{15}$), 5.44 (dd, 1H, J 7.2 and 15.5 Hz, $H^9$). Hydrolysis of the resulting pure acetates (9a), (9b) (10% NaOH/$H_2O$ in THF, 5 h, 20° C.) followed by esterification by diazomethane provided diastereochemically pure ΔHxA$_3$ methyl esters (7a), (7b). More polar epimer of ΔHxA$_3$ (HA-924) (7b) (from less polar ΔHxB$_3$ (6b)): 5.1 mg yield (51%). $R_f$ 0.46 ($C_6H_6$-$Et_2O$, 85:15, 3 developments), mass spectrum of the tBDMSi derivative (m/z, % of related intensity): 431 ([M−OMe]$^+$, 0.18), 405 ([M−t-Bu]$^+$, 4.7), 351 ([$C^1$-$C^{12}$]$^+$, 0.18), 321 ([$C^8$-$C^{20}$]$^+$, 100), 197 (62), 189 ([($C^8$-$C^{20}$)−t-BuMe$_2$SiOH, 17), 171 (27), 75 (79), 73 (83). Less polar epimer of ΔHxA$_3$ (HA-923) (7a) (from more polar ΔHxB$_3$ (6a)): yield is 3.3 mg (33%). $R_f$ 0.50 ($C_6H_6$-$Et_2O$, 85:15, 3 developments), mass spectrum of the tBDMSi derivative (m/z, % of related intensity): 431 (0.06), 405 (1.0), 351 (0.04), 321 (28), 197 (24), 189 (7.3), 171 (12), 75 (56), 73 (100).

EXAMPLE II

The ability of hepoxilin analogs to inhibit agonist-evoked changes in the free intracellular calcium concentration of human neutrophils was assayed.

Human neutrophils were separated from fresh human blood by dextran sedimentation followed by centrifugation on either a Ficoll-Hypaque gradient (Boyum, *J. Clin. Invest.* 21:77–98, 1968) or a discontinuous plasma-Percoll gradient (Downey et al., *J. Appl. Physiol.* 64:728–741, 1988). Residual red blood cells were removed by lysis with $NH_4Cl$ and centrifugation. Washed cells were maintained at room temperature in RPMI 1640 (Sigma Chemical Co., St. Louis, Mo.) without $HCO_3^-$ (buffered to pH 7.3 using 10 mM-Na Hepes) at $10^7$ cells/ml until assayed. For assaying, cells [(1–2)×$10^7$ cells/ml] were suspended in medium containing NaCl (140 nM), KCl (5 nM), $MgCl_2$ (1 nM), $CaCl_2$ (1 nM), Hepes (10 nM) and glucose (10 nM), pH 7.3. The osmolarity of the media was adjusted to 290±5 mosm.

Intracellular free calcium was measured using the fluorescent indicator Indo-1-AM (Molecular Probes, Inc., Eugene, Oreg.). One ml of the freshly prepared neutrophil suspension (10 million cells) was loaded with 3 μl of a 1 mM solution of Indo-1-AM in DMSO (final concentration of the dye being 3 μM) for a period of 30 minutes at 37° C. Tubes were inverted every five minutes. The acetoxymethyl ester (AM) group on the dye allowed its penetration into the cell where esterases cleave it (by saponification) to release the free acid form which is trapped inside the cell. Unloaded dye was removed by centrifugation, and the cells were resuspended in fresh RPMI 1640 (Sigma Chemical Co.). Dye-loaded cells were kept at room temperature on a rotator. For each measurement, 2×$10^6$ cells were added to 1 ml of a clear medium (composition in mM: NaCl 140, KCl 5, $MgCl_2$ 1, $CaCl_2$ 1, Hepes sodium free 10 and glucose 10, pH 7.3, osmolarity 290±5) in a temperature-controlled plastic cuvette (Diamed Lab., Canada) at 37° C. The cell suspension was continuously stirred. Fluorescence was continuously monitored with a Perkin-Elmer fluorescence spectrophotometer, model 650-40 (Perkin-Elmer, Norwalk, Conn.) and recorded on an LKB model 2210 chart recorder (Pharmacia, Sweden) set at 2 cm/min. The excitation wavelength was set at 331 nm, the emission wavelength set at 410 nm, and slits of excitation and emission were set at 3 and 15 respectively. Temperature of the cuvette was maintained at 37° C.±2° C. with (at 37° C.) circulating underneath the cuvette. An equilibrium period of approximately 2 to 5 minutes was allowed before addition of various agents to have a flat baseline signal. Intracellular free calcium was calculated using the following formula:

$$[Ca^{2+}]i = 250\ nM \times \frac{(F - F_{min})}{(F_{max} - F)}$$

All fluorescence values were measured relative to an $MnCl_2$-quenched signal determined as follows: 250 nM is the $K_d$ of Indo-1-AM, F is the relative fluorescence measurement of sample. $F_{max}$ was determined by exposing cells to the calcium ionophore ionomycin (Sigma Chemical Co.) at $10^{-6}$ M final concentration. After $F_{max}$ was determined, $MnCl_2$ at 3 mM final concentration was added to totally quench the Indo-1-AM signal and $F_{Mn}$ was obtained. $F_{min}$ was obtained as follows: $\frac{1}{12} \times (F_{max} - F_{Mn}) + F_{Mn}$. Calibration was performed on each sample. Hepoxilin analogs HxA$_3$ and other agonists (fMLP, PAF, LTB$_4$ and thapsigargin) were added to the cuvette as a 1000× concentrate in DMSO. Hepoxilin analogs HA921–924 were tested first at three concentrations (0.05, 0.1 and 0.5 μg/ml) in DMSO or the DMSO vehicle alone, followed five minutes later by each of the agonists at one concentration, i.e. $HxA_3$, 3 μg/ml; FMLP, $1\times10^{-9}$M; $LTB_4$, 2 ng/ml; PAF, 1 ng/ml and thapsigargin, 100 ng/ml). Alteration of agonist response by the hepoxilin analogs was evaluated by comparison of response in the absence of analog (DMSO vehicle alone) with that observed in the presence of analog.

The results of the assays, shown in the Table, demonstrate that HA-921, HA-922 and HA-923 at the higher concentrations (1.4 μM) inhibit the stimulation of intracellular calcium induced by fMLP, $LTB_4$, hepoxilin $A_3$ and thapsigargin. The analog HA-924 is shown to inhibit hepoxilin $A_3$ and thapsigargin.

TABLE

| Hepoxilin analog | | free $[Ca^{2+}]i$ (nM) | | | |
|---|---|---|---|---|---|
| (μg/ml) | Agonist* | HA-921 | HA-922 | HA-923 | HA-924 |
| 0 | fMLP | 580 | 871 | 741 | |
| 0.05 | " | 260 | 820 | 129 | |
| 0.1 | " | 420 | 461 | 516 | |
| 0.5 | " | 280 | 435 | 161 | |
| 0 | PAF | 800 | 1307 | 645 | |
| 0.05 | " | 980 | 1512 | 806 | |
| 0.1 | " | 840 | 2000 | 806 | |
| 0.5 | " | 440 | 615 | 1516 | |
| 0 | $LTB_4$ | 520 | nd | 290 | |
| 0.05 | " | 340 | 1076 | 548 | |
| 0.1 | " | 580 | nd | 64 | |
| 0.5 | " | 380 | 384 | nd | |
| 0 | $HxA_3$ | 300 | 1333 | 1451 | 638 |
| 0.05 | " | 240 | 333 | 193 | 381 |
| 0.1 | " | 140 | 256 | 193 | 273 |
| 0.5 | " | 320 | 128 | 322 | 26 |
| 0 | Thapsigargin | 1460 | 948 | 774 | 835 |
| 0.05 | " | 840 | 1256 | 2354 | 361 |
| 0.1 | " | 940 | 1051 | 612 | 250 |
| 0.5 | " | 280 | 358 | 225 | 39 |

*Agonist concentrations used were: FMLP, $1\times10^{-9}$M; PAF, 1 ng/mL; $LTB_4$, 2 ng/mL; $HxA_3$, 3 μg/mL; Thapsigargin, 100 ng/mL.

Although the foregoing invention has been described in some detail by way of illustration and example for purposes of clarity of understanding, it will be evident that certain changes and modifications may be practiced within the scope of the appended claims. For example, the synthetic methodology may be modified by the ordinarily skilled practioner to produce other hepoxilin analogs, the activity of which can be readily assayed.

What is claimed is:

1. A compound selected from the group consisting of:

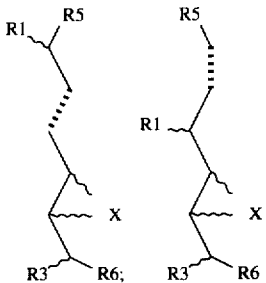

and pharmaceutically acceptable salts thereof, wherein:

X is $C_n$, NH, or S, wherein n is 1, 2, 3 or 4;

R1 is OH, $CH_3$, $CH_2OH$, $N_3$ or $CH_2N_3$;

R3 is H or $CH_3$;

R5 is Y-R2, wherein Y is a six-carbon chain optionally containing up to three double or triple bonds or a mixture of double and triple bonds up to a maximum of three;

R2 is $C_1$-$C_{10}$ alkyl OH, $C_1$-$C_{10}$ alkyl $N_3$ or COOR4;

R4 is H, $C_1$-$C_{10}$ alkyl, $C_5$-$C_6$ cycloalkyl, or $C_5$-$C_6$ aryl;

R6 is a seven-carbon chain optionally containing up to three double or triple bonds or a mixture of double and triple bonds up to a maximum of three; and . . . . . . is a single, double or triple bond.

2. A compound according to claim 1 wherein R2 is alkyl $N_3$, alkyl OH or COOR4, wherein R4 is $C_5$-$C_{10}$ alkyl or $C_5$-$C_6$ aryl.

3. A compound selected from the group consisting of:

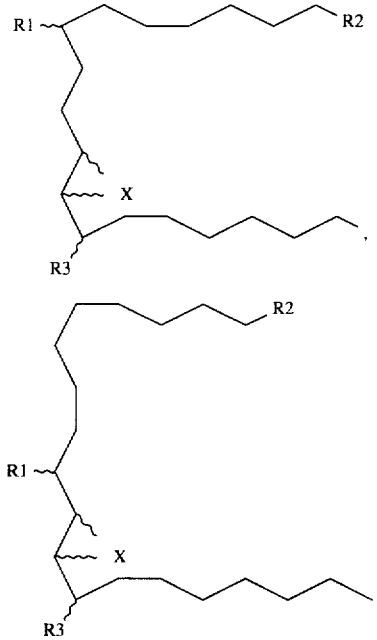

and pharmaceutically acceptable salts thereof, wherein:

X is NH, S or $C_n$, wherein n is 1, 2, 3 or 4;

R1 is OH, $CH_3$, $CH_2OH$, $N_3$ or $CH_2N_3$;

R2 is COOR4, $C_1$-$C_{10}$ alkyl OH or $C_1$-$C_{10}$ alkyl $N_3$;

R3 is H or $CH_3$;

R4 is H, $C_1$-$C_{10}$ alkyl, $C_5$-$C_6$ cycloalkyl or $C_5$-$C_6$ aryl; and

. . . . . . is a single, double or triple bond.

4. A compound according to claim 3 wherein X is $C_n$, NH or S.

5. A compound according to claim 3 wherein X is $C_n$.

6. A compound according to claim 3, wherein X is $CH_2$.

7. A compound according to claim 3, wherein R1 is OH.

8. A compound according to claim 3, wherein R3 is H.

9. A compound according to claim 3, wherein R2 is COOH or $COOCH_3$.

10. A compound according to claim 3 wherein said compound is

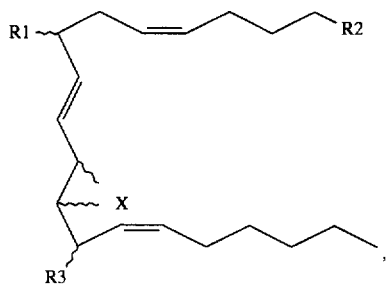
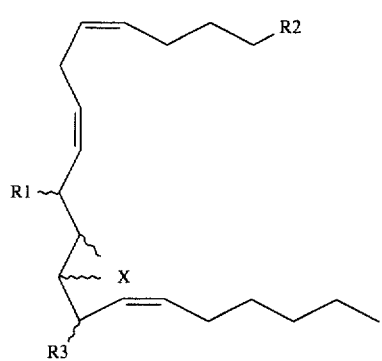
or a pharmaceutically acceptable salt thereof.
11. A compound according to claim 10 wherein said compound is
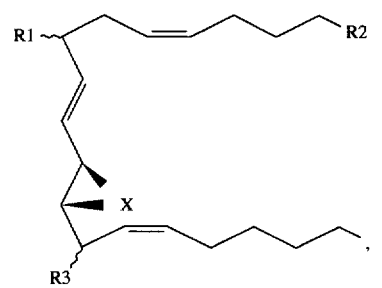
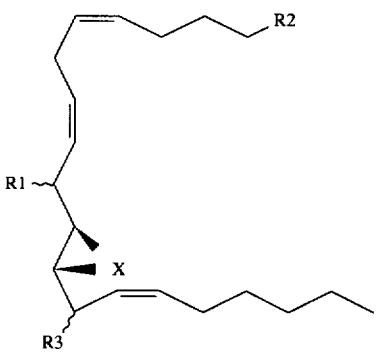
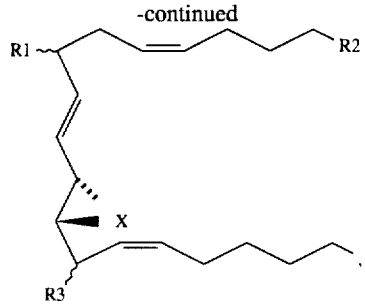
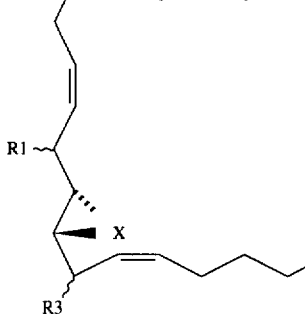
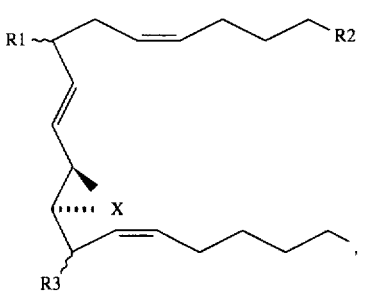
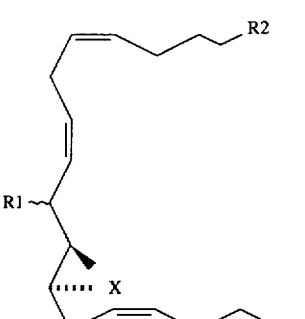
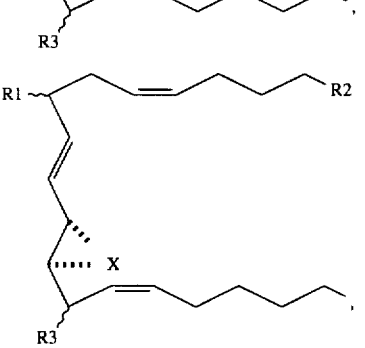

-continued

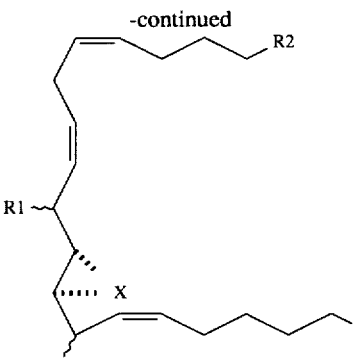

or a pharmaceutically acceptable salt thereof.

12. A compound according to claim 11 wherein X is $C_n$, NH or S; R1 is OH; $R_2$ is COOH or COOCH$_3$ and R3 is H.

13. A compound according to claim 3 wherein R4 is $C_5$-$C_{10}$ alkyl, $C_5$-$C_6$ cycloalkyl or $C_5$-$C_6$ aryl.

14. A compound according to claim 3 wherein X is O and R2 is alkyl $N_3$ or alkyl OH.

15. A compound according to claim 3 wherein R2 is alkyl $N_3$ or alkyl OH.

16. A compound selected from the group consisting of:

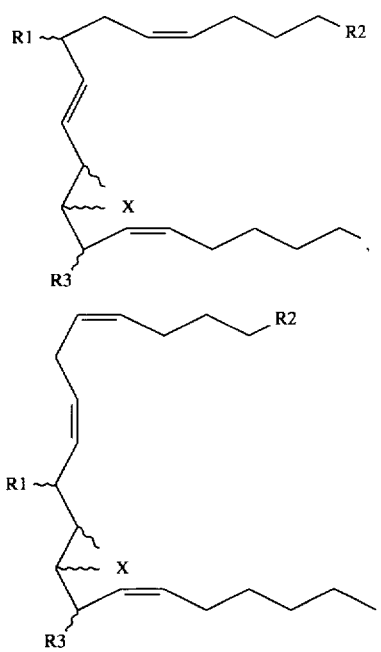

and pharmaceutically acceptable salts thereof, wherein:
X is NH, S or $C_n$, wherein n is 1, 2, 3 or 4;
R1 is OH, CH$_3$, CH$_2$OH, N$_3$ or CH$_2$N$_3$;
R2 is COOR4;
R3 is H or CH$_3$; and
R4 is H or lower alkyl.

17. A compound according to claim 16 wherein X is $C_n$.

18. A compound according to claim 17 wherein R1 is OH, R2 is COOH or COOCH$_3$, and R3 is H.

19. A compound according to claim 16 wherein R1 is OH, R2 is COOH or COOCH$_3$, and R3 is H.

20. A compound selected from the group consisting of:

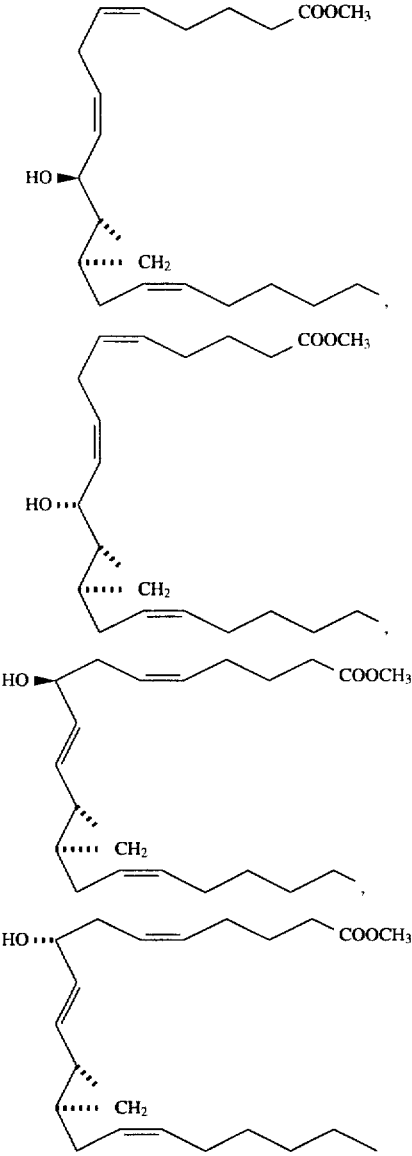

and pharmaceutically acceptable salts thereof.

21. A pharmaceutical composition comprising a compound according to claim 1 in combination with a pharmaceutically acceptable vehicle.

* * * * *

UNITED STATES PATENT AND TRADEMARK OFFICE
CERTIFICATE OF CORRECTION

PATENT NO.  : 5,616,607
DATED       : April 1, 1997
INVENTOR(S) : C. R. Pace-Asciak It is certified that error appears in the above-indentified patent and that said Letters Patent is hereby corrected as shown below:

Claim 3, delete the formulas and insert therefor:

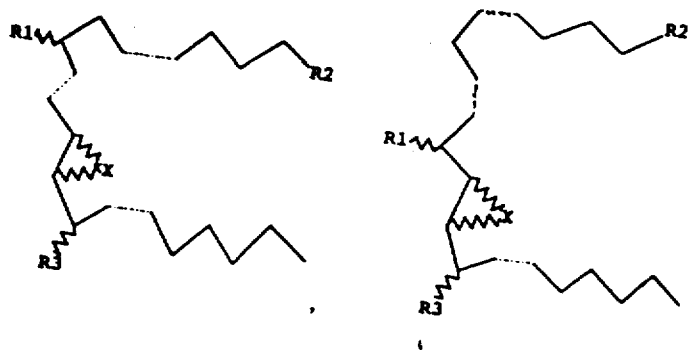

Signed and Sealed this

Nineteenth Day of August, 1997

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,616,607
DATED : April 1, 1997
INVENTOR(S) : C. R. Pace-Asciak

It is certified that error appears in the above-identified patent and that said Letters Patent is hereby corrected as shown below:

Change claim 14 to read as follows:

--14. A compound according to claim 13 wherein  is a double bond--

Signed and Sealed this

Twenty-fifth Day of May, 1999

Attest:

Q. TODD DICKINSON

Attesting Officer     Acting Commissioner of Patents and Trademarks